US012076355B2

(12) United States Patent
Lin et al.

(10) Patent No.: US 12,076,355 B2
(45) Date of Patent: Sep. 3, 2024

(54) COMPOSITION AND METHOD FOR TREATING CANCER

(71) Applicants: National Yang Ming Chiao Tung University, Taipei (TW); National Research Institute of Chinese Medicine, Ministry of Health and Welfare, Taipei (TW)

(72) Inventors: Tung-Yi Lin, Taipei (TW); Mei-Kuang Lu, Taipei (TW)

(73) Assignees: National Yang Ming Chiao Tung University, Taipei (TW); National Research Institute of Chinese Medicine, Ministry of Health and Welfare, Taipei (TW)

( * ) Notice: Subject to any disclaimer, the term of this patent is extended or adjusted under 35 U.S.C. 154(b) by 0 days.

(21) Appl. No.: 17/993,343

(22) Filed: Nov. 23, 2022

(65) Prior Publication Data

US 2023/0165917 A1 Jun. 1, 2023

Related U.S. Application Data

(60) Provisional application No. 63/283,420, filed on Nov. 26, 2021.

(51) Int. Cl.

| | |
|---|---|
| ***A61K 36/07*** | (2006.01) |
| ***A61K 31/737*** | (2006.01) |
| ***A61P 35/00*** | (2006.01) |

(52) U.S. Cl.

CPC ............ *A61K 36/07* (2013.01); *A61K 31/737* (2013.01); *A61P 35/00* (2018.01)

(58) Field of Classification Search

None

See application file for complete search history.

(56) References Cited

PUBLICATIONS

Tsai, MY., Hung, YC., Chen, YH. et al. A preliminary randomised controlled study of short-term Antrodia cinnamomea treatment combined with chemotherapy for patients with advanced cancer. BMC Complement Altern Med 16, 322 (2016). (Year: 2016).*

* cited by examiner

*Primary Examiner* — Blaine Lankford

(74) *Attorney, Agent, or Firm* — Fox Rothschild LLP

(57) ABSTRACT

Provided is a method for preventing or treating cancer in a subject in need thereof, including administering to the subject an effective amount of a composition including a fraction of polysaccharide isolated from *Antrodia cinnamomea* cultured in the presence of zinc sulfate and a carrier thereof, wherein the polysaccharide includes glucose and fucose. Also provided are a method for preparing the composition and a composition including the polysaccharide fraction obtained therefrom.

15 Claims, 21 Drawing Sheets

COMPOSITION AND METHOD FOR TREATING CANCER

BACKGROUND

1. Technical Field

The present disclosure relates to a composition comprising sulfated polysaccharides isolated from *Antrodia cinnamomea* and its use in preventing and treating or ameliorating malignant diseases, such as cancer. Also provided herein are methods of activating of an immune cell and increasing immunity of an immune cell against malignant cells. The present disclosure also relates to a method for preparing the composition from cultured *Antrodia cinnamomea.*

2. Description of Associated Art

Cancers remain the leading causes of death worldwide. International Agency for Research on Cancer (IARC) estimated 10 million deaths and 19.3 million cases in 2020 in the recently released updates in GLOBOCAN 2020. Developing novel cancer therapy or improving the efficacy of current cancer treatment therefore has long since been the prime goal of the medical community. While under accumulated efforts, many types of cancer therapies are currently available, including chemotherapy, surgery, radiation therapy, hormone therapy, biologic therapy, targeted therapy, and most recently, immunotherapy and cell-based therapy; however, cancer still poses enormous risk to human health and a burden to the health economics.

Two of the main concerns on the current cancer therapies are limited efficacy and side effects that cause discomfort and sometimes even harm to the body, and the medical community is constantly in search of methods and pharmaceutical agents that treat cancer safely and effectively.

SUMMARY

The present disclosure provides a method for preventing or treating cancer in a subject in need thereof, comprising administering to said subject an effective amount of a composition comprising a fraction of polysaccharide isolated from *Antrodia cinnamomea* cultured in presence of zinc sulfate and a carrier thereof, wherein the polysaccharide comprises glucose and fucose. In at least one embodiment, the zinc sulfate is between 1 μM to 100 μM. In some embodiments, the zinc sulfate is about 10 μM.

In at least one embodiment, the polysaccharide isolated from *Antrodia cinnamomea* is sulfated polysaccharide. In at least one embodiment, the sulfated polysaccharide further contains at least one of galactosamine, glucosamine, galactose and mannose. In at least one embodiment, glucose has the highest weight ratio in the sulfated polysaccharide. In another embodiment, the weight ratio of glucose to fucose is 1,000:1 to 150:1, or the weight ratio of glucose to galactosamine is 3,000:1 to 250:1, or the weight ratio of glucose to glucosamine is 80:1 to 25:1, or the weight ratio of glucose to galactose is 10:1 to 20:1, or the weight ratio of glucose to mannose is 200:1 to 20:1.

In at least one embodiment, the polysaccharide has a molecular weight between 1 kDa and 100 kDa. In some embodiments, the polysaccharide has a molecular weight between 1 kDa and 20 kDa. In some embodiments, the polysaccharide has an average molecular weight of about 8 kDa.

In the present disclosure, the cancer to be treated by the provided composition is a cancer involving signal transduction through EGFR or TGFβRI. In at least one embodiment, the cancer is lung cancer, lung adenocarcinoma, non-small cell lung adenocarcinoma, gastric cancer, urothelial carcinoma, breast cancer, brain cancer, glioma, renal cancer, head and neck cancer or colorectal cancer. In some embodiments, the cancer has wild-type EGFR.

The present disclosure further provides a method for preparing a composition, comprising culturing *Antrodia cinnamomea* in presence of zinc sulfate; isolating polysaccharide from *Antrodia cinnamomea*; and obtaining a fraction of the polysaccharide having glucose and fucose. In some embodiments, the present disclosure provides a composition prepared by the aforementioned method.

In at least one embodiment, the method of the present disclosure further comprises contacting the immune cell with the composition of the present disclosure to activate the immune cell. In at least one embodiment, the immune cell activation is in vitro or in vivo. In some embodiments, the immune cell is a phagocyte including neutrophil, monocyte, macrophage, mast cell or dendritic cell.

BRIEF DESCRIPTION OF THE DRAWINGS

The present disclosure can be more fully understood by reading the following detailed descriptions of the embodiments, with reference made to the accompanying drawings, wherein:

FIG. 4A shows colony formation of A549 and H1975 cells treated with ZnF3 (400 μg/mL) for 5 days, normalized against an untreated control group (CTL). FIG. 4B shows cell cycle distribution, and FIG. 4C shows percentage of apoptotic cells measured by flow cytometry after treated with ZnF3 (400 μg/mL) for 48 h. The data were collected from three separate experiments and presented as a mean±SD: error bars indicated SDs. Statistically significant differences are shown as * $P<0.05$ and *** $P<0.001$ compared with the control group (CTL);

FIG. 7A shows viability of Raw264.7 cells after ZnF3 treatment. Each experimental group is normalized against an untreated control group. FIG. 7B and FIG. 7C show the levels of TNF-α and IL-6, respectively, determined by ELISA. FIG. 7D shows the amount of NO production measured by a Griess assay. Each experimental group is normalized against control (LPS stimulation). FIG. 7E shows schematic design of in vitro ZnF3-stimulated Raw264.7 cells experiments. Raw264.7 cells were stimulated with ZnF3 for 24 h. The conditional medium was harvested and then added to LLC1-GFP cells for 48 h. The viability of LLC1-GFP cells was determined using the intensity of green fluorescence shown under microscope (FIG. 7F), which was quantified and presented in histograms shown in FIG. 7G. The data were collected from three separate experiments and presented as a mean #SDs: the error bars indicate SD. Significant differences are shown as * $P<0.05$ and *** $P<0.001$, compared with control;

FIG. 8A shows percentage of phagocytosis in cells stimulated with various concentrations of ZnF3 (0 to 25 μg/mL) for 24 h compared to non-treated cells. FIG. 8B shows the schematic design of the in vitro co-culture experiment of ZnF3-stimulated Raw264.7 cells and LLC1-GFP cells. LLC1-GFP cells were co-cultured with Raw264.7 cells and were stimulated with ZnF3 for 24 and 48 h. The viability of LLC1-GFP cells was determined using the intensity of green fluorescence shown under microscope (FIG. 8C), which was quantified and presented in histograms shown in FIG. 8D. Each experimental group is normalized against an untreated control group. The data were collected from three separate experiments and presented as a mean±SDs: the error bars indicated SD. Significant differences are shown as * $P<0.05$ and *** $P<0.001$, compared with the control group.

FIG. 9A shows representative histograms of M1-phenotype surface marker (CD86, CD80, CD64, and MHCII) in RAW264.7 cells. FIG. 9B shows representative histograms of M2-phenotype surface marker (CD206) in RAW264.7 cells. FIG. 9C shows quantitative analysis of M1 or M2 surface markers in RAW264.7 treated with ZnF3. The data were collected from three separate experiments and is presented as a mean #SDs: the error bars indicated SD. Significant differences are shown as *** $p<0.001$, compared with the control group).

DETAILED DESCRIPTION OF THE EMBODIMENTS

Figure 1A:
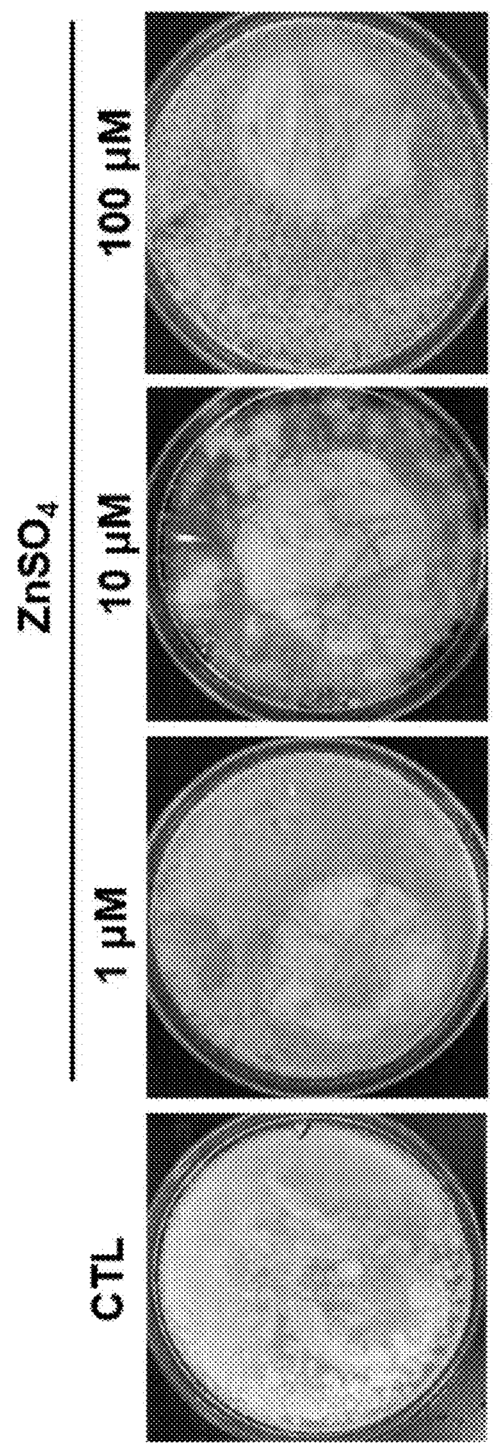
FIGS. 1A to 1C show the effect of zinc sulfate on the phenotype (FIG. 1A), biomass (FIG. 1B) and SPS yields (FIG. 1C) of *A. cinnamomea* cultured for 49 days. * $P<0.05$ compared with the control group without zinc sulfate.

Sulfated polysaccharide (SPS) is a class of natural polysaccharides with modified sulfate bonds that are mainly found in connective tissue of invertebrates. SPS is shown to exhibit several bioactivities and is non-cytotoxic. However, the bioactivity of SPS from different species depends upon its monosaccharide composition, position of the sulfate modification, degree of sulfation, molecular weight and solubility in water.

*Antrodia cinnamomea* (*A. cinnamomea*) belongs to Polyporaceae which grows on the brown heartwood of *Cinnamomum kanehirae*. The active components of *A. cinnamomea* have been identified, and include polysaccharides and terpenoids. Polysaccharides in *A. cinnamomea* mycelium have two types, including SPS and non-sulfated polysaccharides (NSPS). However, yield and bioactivity of SPS from *A. cinnamomea* are both less than optimal. The present disclosure provides a method for the cultivation of *A. cinnamomea* and obtains a SPS fraction with physiochemistry and bioactivities for an anti-cancer agent.

Zinc is a necessary microelement that controls multiple physiological responses in plants and animals. Currently, zinc sulfate is used in agricultural fertilizer acting as mineral salts, animal feeds and male nutritional supplements. It has been shown that SPS from *A. cinnamomea* treated with high concentrations (mM) of zinc sulfate does not demonstrate significant immune-modulation or anti-cancer properties. Also, the yield and anti-cancer activity of SPS have not been determined. In the present disclosure, low concentrations of zinc sulfate are adopted for cultivation of *A. cinnamomea* and isolation of a polysaccharide with biological activity.

The present disclosure determines the effect of low concentrations (μM) of zinc sulfate on the yield and biological activity of SPSs in *A. cinnamomea*. The identified SPSs are further fragmented, and the effective fragments of SPS with anti-cancer activity are identified. In the present disclosure, the identified polysaccharide fraction, ZnF3, effectively inhibits tumor cell growth by inducing apoptosis. The present disclosure further explores the effect of low-dose ZnF3 (e.g., 25 μg/mL) on macrophages, and it is found that ZnF3 activates macrophages and consequently inhibits cancer cells.

All terms including descriptive or technical terms which are used herein should be construed as having meanings that are obvious to one of ordinary skill in the art. However, the terms may have different meanings according to an intention of one of ordinary skill in the art, case precedents, or the appearance of new technologies. Also, some terms may be arbitrarily selected by the applicant, and in this case, the meaning of the selected terms will be described in detail in the descriptions of the present disclosure. Thus, the terms used herein are defined based on the meaning of the terms together with the descriptions throughout the specification.

It is further noted that, as used in this disclosure, the singular forms "a," "an," and "the" include plural referents unless expressly and unequivocally limited to one referent. The term "or" is used interchangeably with the term "and/or" unless the context clearly indicates otherwise.

Also, when a part "includes" or "comprises" a component or a step, unless there is a particular description contrary thereto, the part can further include other components or other steps, not excluding the others.

The terms "subject," "patient," and "individual" are used interchangeably herein and may encompass any vertebrate including, but not limited to, mammals, reptiles, amphibians, and/or fish that are afflicted with, suspected of having, at risk for, pre-disposed to, or screened for a disease, disorder, or syndrome (e.g., cancer). Preferably, the "subject" may be a human, but may also be another animal such as a domestic animal (e.g., a dog, a cat, or the like), a farm animal (e.g., a cow, a sheep, a pig, a horse, or the like), or a laboratory animal (e.g., a monkey, a rodent, a murine, a rabbit, a guinea pig, or the like).

The terms "to treat" and "to ameliorate" as used herein mean the action taken for management and care of a patient for the purpose of combating a disease, disorder or condition. The term is intended to include the delaying of progression of the disease, disorder or condition, the alleviation or relief of symptoms and complications, and/or the cure or elimination of the disease, disorder or condition. The patient to be treated may be a mammal, e.g., a human being.

The terms "malignant disease," "malignant condition," "malignancy" or "cancer" are used interchangeably herein and refer to a malignant neoplasm. The terms "neoplasm" and "tumor" are used herein interchangeably and refer to an abnormal mass of tissue, wherein the growth of the mass surpasses and is not coordinated with the growth of a normal tissue. A "neoplasm" or "tumor" may be "benign" or "malignant," depending on the following characteristics: degree of cellular differentiation (including morphology and functionality), rate of growth, local invasion, and metastasis. A "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. Malignant neoplasms or cancers include, but are not limited to: acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancer (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumor; immunocytic amyloidosis; kidney cancer (e.g., nephroblastoma (also known as Wilms' tumor), renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) (also known as myelofibrosis (MF)), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), islet cell tumor); penile cancer (e.g., Paget's disease of the penis and scrotum); pinealoma; primitive neuroectodermal tumor (PNT); plasma cell neoplasia; paraneoplastic syndrome; intraepithelial neoplasm: prostate cancer (e.g., prostate adenocarcinoma): rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva). In some embodiments of the present disclosure, said cancers are selected from cancer involving signaling transduction through EGFR or TGFβRI, including lung cancer, lung adenocarcinoma, non-small cell lung adenocarcinoma, gastric cancer, urothelial carcinoma, breast cancer, brain cancer, head and neck cancer or colorectal cancer.

The "effective amount" described in the present disclosure represents the amount of an active ingredient (e.g., a polysaccharide fraction isolated from *Antrodia cinnamomea*) that is required to confer a desired therapeutic effect (e.g., inducing apoptosis of cancer cells and/or activating immunity against cancer cells, thereby treating cancer in the subject). The effective amount may vary depending on the organism or individual treated but can be determined experimentally using various techniques, including a dose escalation study.

EXAMPLES

Exemplary embodiments of the present disclosure are further described in the following examples, which should not be construed to limit the scope of the present disclosure.

The cells and cell cultures used in the following examples include two human lung adenocarcinoma cells, A549 and H1975, which were purchased from the American Type Culture Collection (ATCC, USA) and Elabscience Biotechnology Inc. (USA), respectively. In addition, mouse Lewis lung carcinoma LLC1, macrophage Raw264.7 and normal lung fibroblast MRC-5 cells were purchased from the Bioresource Collection and Research Center (BCRC, Taiwan). Cancer cells were cultured as described in Lin et al., Cancer Lett. 375(2) (2016) 340-8. Raw264.7 cell was maintained in Dulbecco's modified Eagle medium (DMEM; GIBCO/Life Technologies) supplemented with 5% heat-inactivated fetal bovine serum (FBS), 100 units/mL of penicillin and streptomycin (Biological industries, Cromwell, CT) and 3.7 g/L of $NaHCO_3$. MRC-5 cell was cultured in minimum essential medium (MEM; GIBCO/Life Technologies) supplemented with 2 mM L-glutamine, 1.5 g/L sodium bicarbonate, 0.1 mM non-essential amino acids, 1.0 mM sodium pyruvate and 10% FBS. All cells were maintained at 37° C. in a humidified atmosphere of 5% $CO_2$.

Regarding statistical analysis, all of the data are expressed as the mean±standard deviation. Data from the three independent experiments for two groups were analyzed for statistical significance using a t-test and GraphPad Prism8 software. * indicates a p-value of less than 0.05 and statistical significance.

Preparation Example 1: Culturing of *Antrodia cinnamomea* (*A. cinnamomea*) and Isolation of Sulfated Polysaccharide (SPS)

The mycelia of *A. cinnamomea* B86 were cultured in a basal medium containing 100 mL of 24 g/L potato-dextrose-broth (PDB), 20 g/L glucose, and zinc sulfate at different concentrations (1, 10 and 100 μM) at pH 5.6 for 49 days. At the end of incubation, the mycelia were harvested as described in Lin et al., Carbohydr. Polym. 210 (2019) 175-184. The phenotypes of mycelial of *A. cinnamomea* cultured under various concentrations of zinc sulfate are shown in FIG. 1A. Compared with the control, the mycelia that were fed with 1 to 100 μM zinc sulfate were more orange-red in color, remained alive and showed no retardation in growth.

Figure 1C:
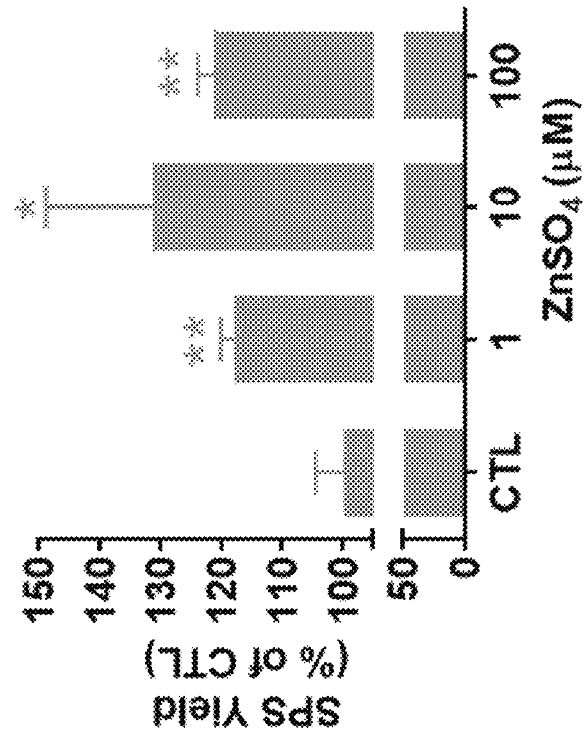
Figure 1B:
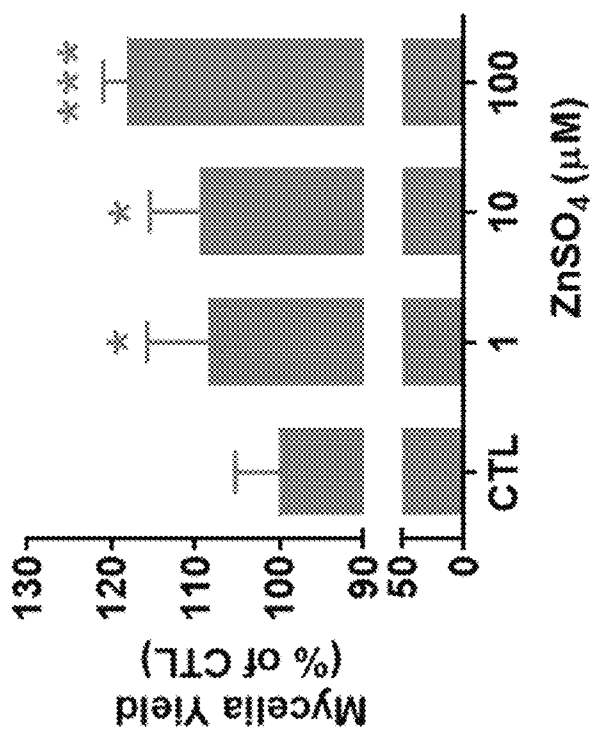

Following the methods of Albano & Mourao (1986) and Lin et al., Carbohydr. Polym. 210 (2019) 175-184, sulfated polysaccharides (SPS) were isolated from mycelia of *A. cinnamomea* treated with various concentrations (1, 10 and 100 μM) of zinc sulfate for 49 days. The biomass of mycelia and yield of the isolated SPS were determined. As shown in FIG. 1B, a direct dosage effect was shown on the biomass of mycelia, indicating that zinc sulfate at concentrations 1, 10 and 100 μM all effectively induced growth of mycelia. Regarding the yield of the isolated SPS, zinc sulfate at concentrations 1, 10 and 100 μM all effectively increased SPS yield, as shown in FIG. 1C. For example, treating the *A. cinnamomea* culture with 10 μM zinc sulfate obtained a SPS yield of 130% relative to the control group.

Preparation Example 2: Fractionation and Characterization of SPS from *A. cinnamomea*

40 mg of SPS powder isolated from *A. cinnamomea* mycelia cultured with 10 μM $ZnSO_4$ (denoted as $ZnSO_4$-10) were dissolved in 3 mL of NaCl (150 mM) buffer at pH 6.8 containing $NaH_2PO_4$ (10 mM) and chromatographed using an open column of Fractogel BioSec (103×1.5 cm; Merck). Fractions of 2.8 mL/tube were harvested and were identified for hexose using the phenol-sulfuric acid method, as shown in DuBois et al., Analytical Chemistry 28(3) (1956) 350-356. The absorbance was measured at 488 nm and recorded as the hexose content. Authentic standards of dextran series (Sigma-Aldrich) containing average molecular weights of $69.8\times10^3$, $40.0\times10^3$ and $10.5\times10^3$ Daltons (Da) were used as the calibration curve.

The molecular weight and monosaccharide compositions of the obtained SPS fractions were determined by the size-exclusion chromatography (SEC) column and high-performance anion-exchange chromatography (HPAEC; Dionex BioLC), respectively. The detailed procedures for analyzing molecule weight, monosaccharide compositions and sulfate content were adopted from Lin et al., Carbohydr. Polym. 216 (2019) 204-212. In addition, the liberated sulfate ions in the SPSs were measured following the previous methods as disclosed in Lu et al., Carbohydr. Polym. 202 (2018) 536-544 and Saito et al., Journal of Biological Chemistry 243(7) (1968) 1536-1542.

Figure 2:
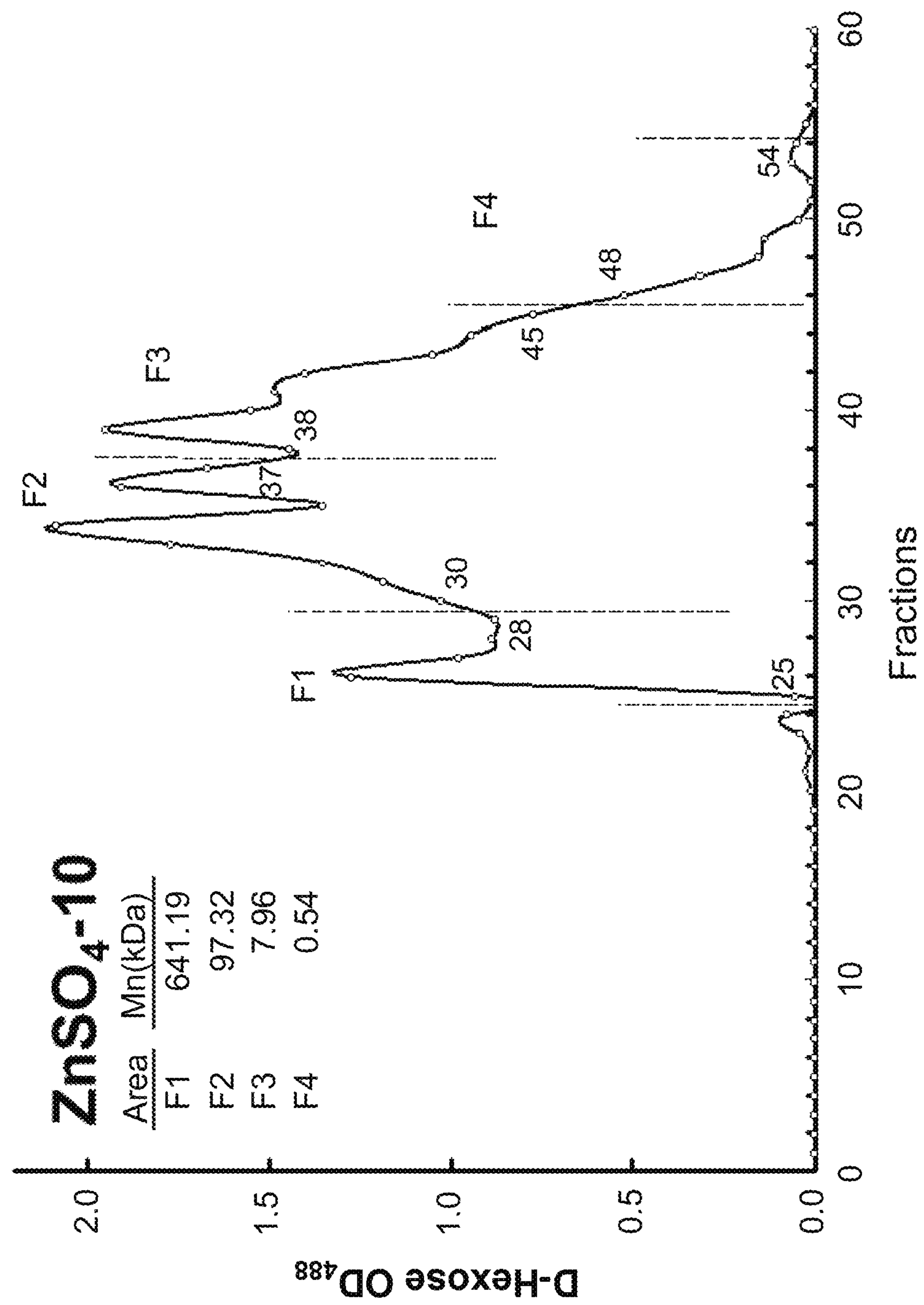
FIG. 2 shows fractionation of SPS from *A. cinnamomea* B86 cultured with 10 μM zinc sulfate ($ZnSO_4$-10) for 49-days. SPSs are fractionated by gel filtration column chromatography into four fractions: F1 containing fractions 25 to 29; F2 containing fractions 30 to 37: F3 containing fractions 38 to 44; and F4 containing fractions 45 to 54. A lyophilized preparation containing SPS was dissolved in a 5 mL buffer containing 150 mM NaCl and 10 mM $NaH_2PO_4$ at pH6.8 and was chromatographed using a BioSec 103×1.5 cm column (Merck). The flow rate was 0.8 mL/min. The column effluent was measured using a phenol-sulfuric acid assay (488 nm) for D-hexose.

As shown in FIG. 2, the isolated SPSs were divided into four fractions and denoted as ZnF1, ZnF2, ZnF3 and ZnF4. The estimated Mn values (average molecular weight) for each SPS fraction ZnF1, ZnF2, ZnF3 and ZnF4 are 641.19, 97.32, 7.96, and 0.54 kDa, respectively.

The monosaccharide composition of each fractionated SPS was determined by HPAEC. As shown in Table 1 below, sorbitol, fucose, galactose, glucosamine, glucose and mannose are the major neutral sugars in each fractionated SPS. For example, glucose is the predominant species and is present in the ZnF1, ZnF2 and ZnF3 at an amount of 1,289, 564 and 693 μmol/g SPS, respectively.

Also shown in Table 1 below, the sulfate content of each fractionated SPS was determined, and the results show that ZnF3 and ZnF4 contain high sulfate contents at 1.35 and 1.56 mmol/g SPS, respectively. Compared to a previous study which shows a low sulfate content of 0.74 μmol/g SPS in B86-III, the first SPS isolated from *A. cinnamomea* (Lu et al., Carbohydr. Polym. 167 (2017) 229-239), the contents of sulfate in ZnF3 and ZnF4 have increased by more than a thousand times.

The above results suggest that zinc sulfate at concentrations of 1, 10 and 100 μM increases production of SPS in *A. cinnamomea*. In addition, a fraction of isolated SPS such as ZnF3 contains a significantly higher content of glucosamine and mannose than other fractions ZnF1, ZnF2 or ZnF4.

TABLE 1

| Chemical compositions of fractionated *A. cinnamomea* SPS cultured with 10 μM $ZnSO_4$ | | | | |
|---|---|---|---|---|
| | ZnF1 | ZnF2 | Zn F3 | ZnF4 |
| | Neutral sugars (μmol/g SPS) | | | |
| Myo-inositol | — | 9.50 ± 0.23 | 7.93 ± 0.17 | 21.85 ± 0.91 |
| Sorbitol | 30.98 ± 0.63 | 19.21 ± 0.03 | 23.36 ± 0.37 | 24.57 ± 0.02 |
| Fucose | 1.36 ± 0.13 | 4.26 ± 0.24 | 3.85 ± 0.25 | 1.17 ± 0.06 |
| Galactosamine | 0.51 ± 0.01 | 0.31 ± 0.04 | 2.47 ± 0.01 | 23.95 ± 0.16 |
| Glucosamine | 17.09 ± 0.26 | 17.13 ± 0.02 | 23.84 ± 0.16 | 7.52 ± 0.07 |
| Galactose | 90.78 ± 0.73 | 166.04 ± 0.43 | 45.95 ± 0.31 | — |
| Glucose | 1289.69 ± 11.59 | 563.91 ± 1.02 | 692.51 ± 12.51 | 24.94 ± 0.30 |
| Mannose | 7.08 ± 0.73 | 10.45 ± 0.44 | 30.60 ± 0.18 | 2.81 ± 0.22 |
| Fructose | — | — | — | 3.26 ± 0.29 |
| | Sulfate (mmol/g SPS) | | | |
| | 0.95 ± 0.01 | 0.40 ± 0.01 | 1.35 ± 0.02 | 1.56 ± 0.01 |

Example 1: Effect of SPS on Cancer Cell Viability

To determine the anti-cancer activity of SPS isolated from *A. cinnamomea* treated with various concentrations of zinc sulfate, cell viability of human lung cancer cells A549 was determined by a 3-(4,5-dimethylthiazole-2-yl)-2,5-diphenyl tetrazolium bromide (MTT) assay. For example, cells were seeded in triplicate on a 96-well plate at a density of $3\times 10^5$ cells in each well, prior to treatment with various concentrations (0 to 800 μg/mL) of the SPS fractions (ZnF1 to ZnF4) for 48 h. After treatment, all samples were incubated with 10 μL MTT dye (10 mg/mL) for 4 h, as previously described in Lin et al., Carbohydr. Polym. 216 (2019) 204-212 and Lin et al., Carbohydr. Polym. 210 (2019) 175-184. The medium was then mixed with DMSO, and the absorbance was measured on a microplate reader at 570 nm.

As shown in Table 2 below, SPS isolated from *A. cinnamomea* treated with zinc sulfate inhibits cell viability of A549 cells. For example, SPS from 10 UM zinc sulfate-treated *A. cinnamomea* showed the maximum inhibition of A549 and achieved a more than 20% of cancer cell inhibition at an amount as low as 50 μg/mL. These results show that mycelia of *A. cinnamomea* cultured with 10 UM zinc sulfate exhibit highly effective biological activity.

TABLE 2

| Viability of A549 cells treated with SPS isolated from $ZnSO_4$-treated *A. cinnamomea* | | | | | | |
|---|---|---|---|---|---|---|
| $ZnSO_4$ treatment | Cell viability (%) of A549 cells treated with SPS (μg/mL) | | | | | |
| (μM) | 0 | 50 | 100 | 200 | 400 | 800 |
| 1 | 100.0% | 96.0% | 90.6% | 88.4% | 84.0% | 83.1% |
| 10 | 100.0% | 77.5% | 76.2% | 74.3% | 67.9% | 65.4% |
| 100 | 100.0% | 89.2% | 87.9% | 87.0% | 82.4% | 79.6% |

Figure 3:
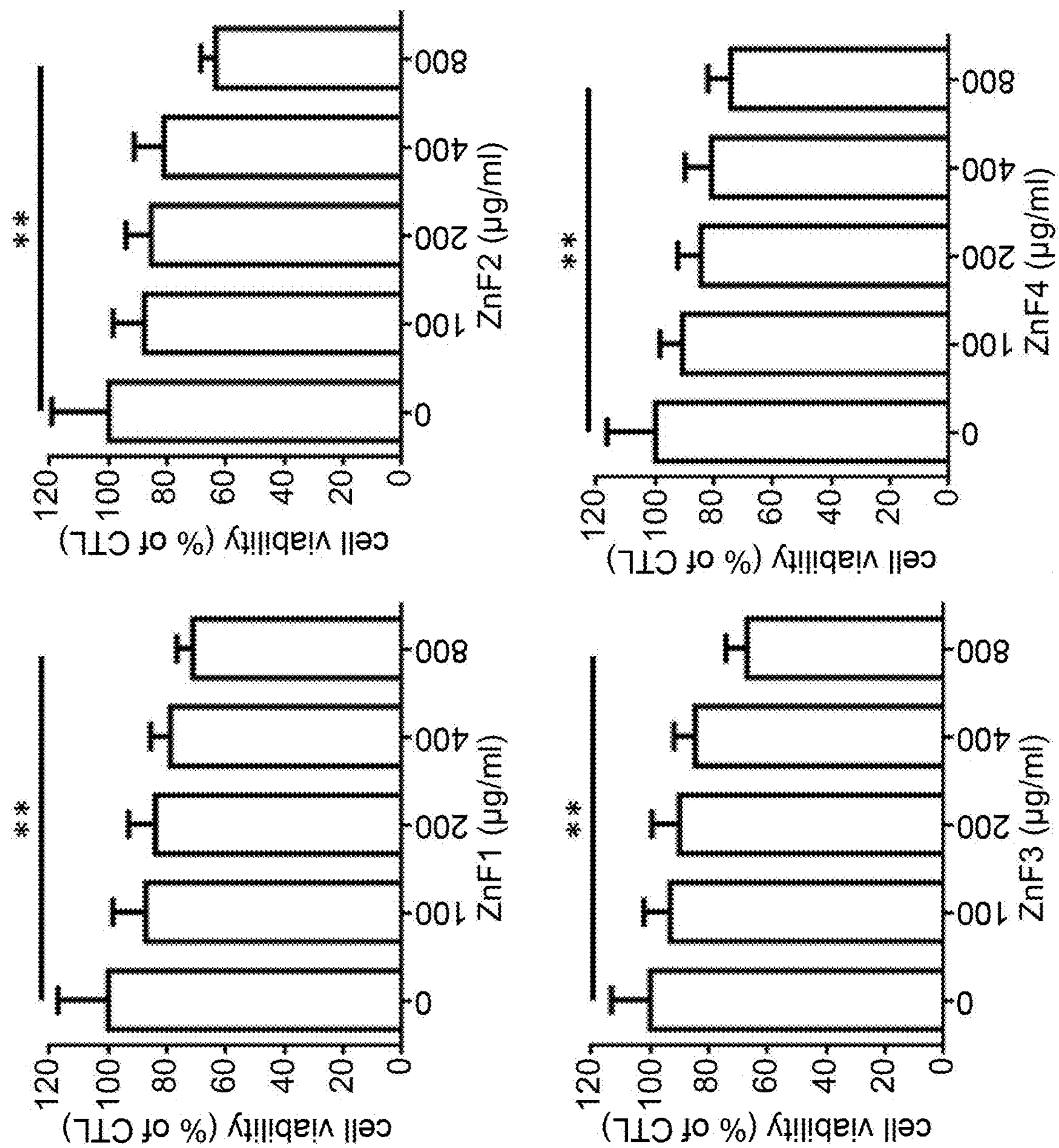
FIG. 3 shows the inhibition of cell viability of lung cancer A549 cells by fractionated SPS. A549 cells were treated with various doses (0 to 800 μg/mL) of fractionated SPS (ZnF1 to ZnF4) isolated from 10 UM zinc sulfate-treated *A. cinnamomea* for 48 h. The viability of the cells was then determined using MTT assays. Each group of SPS-treated samples was normalized against an untreated control group (CTL). The data were collected from three separate experiments and presented as a mean±SD: error bars indicated SDs. Statistically significant differences are shown (** $P<0.01$ compared with CTL)

A549 cell viability was further examined with different individual SPS fractions ZnF1 to ZnF4 isolated from $ZnSO_4$ (10 μM)-treated *A. cinnamomea*. As shown in FIG. 3, all SPS fractions exhibit anti-cancer activity in A549 cells, inhibiting cell viability by about 15% to 20% after 48 h of treatment (at 400 μg/mL). ZnF2 and ZnF3 inhibit cell viability by about 35% after 48 h of treatment (at 800 μg/mL), compared to the untreated cells (control, CTL).

Figure 4A:
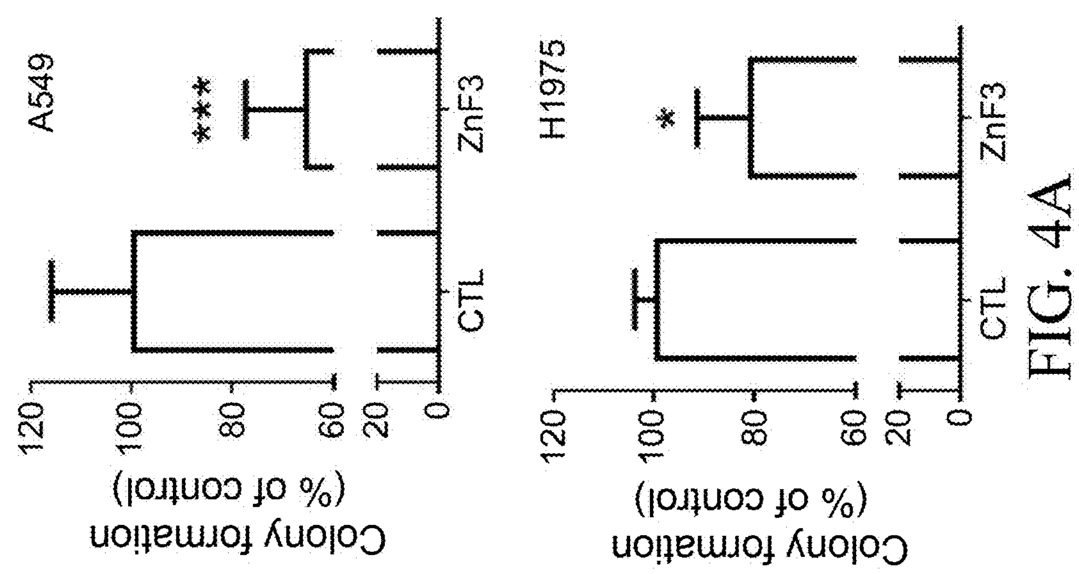
FIGS. 4A to 4C show inhibition of the viability of A549 and H1975 cells by ZnF3.

Example 2: SPS Fraction ZnF3 Disrupts Cell Cycle Distribution and Induces Apoptosis in Cancer Cells To determine the effect of SPS fraction ZnF3 on cancer cells, lung cancer A549 and H1975 cells, which harbor mutant Kirsten rat sarcoma viral oncogene homologue (KRAS) and epidermal growth factor receptor (EGFR), respectively, were used. As shown in FIG. 4A, ZnF3 inhibits the formation of colonies of A549 and H1975 cells. Specifically, ZnF3 inhibits 40% colony formation of A549 cells and 25% colony formation in H1975 cells.

Figure 4B:
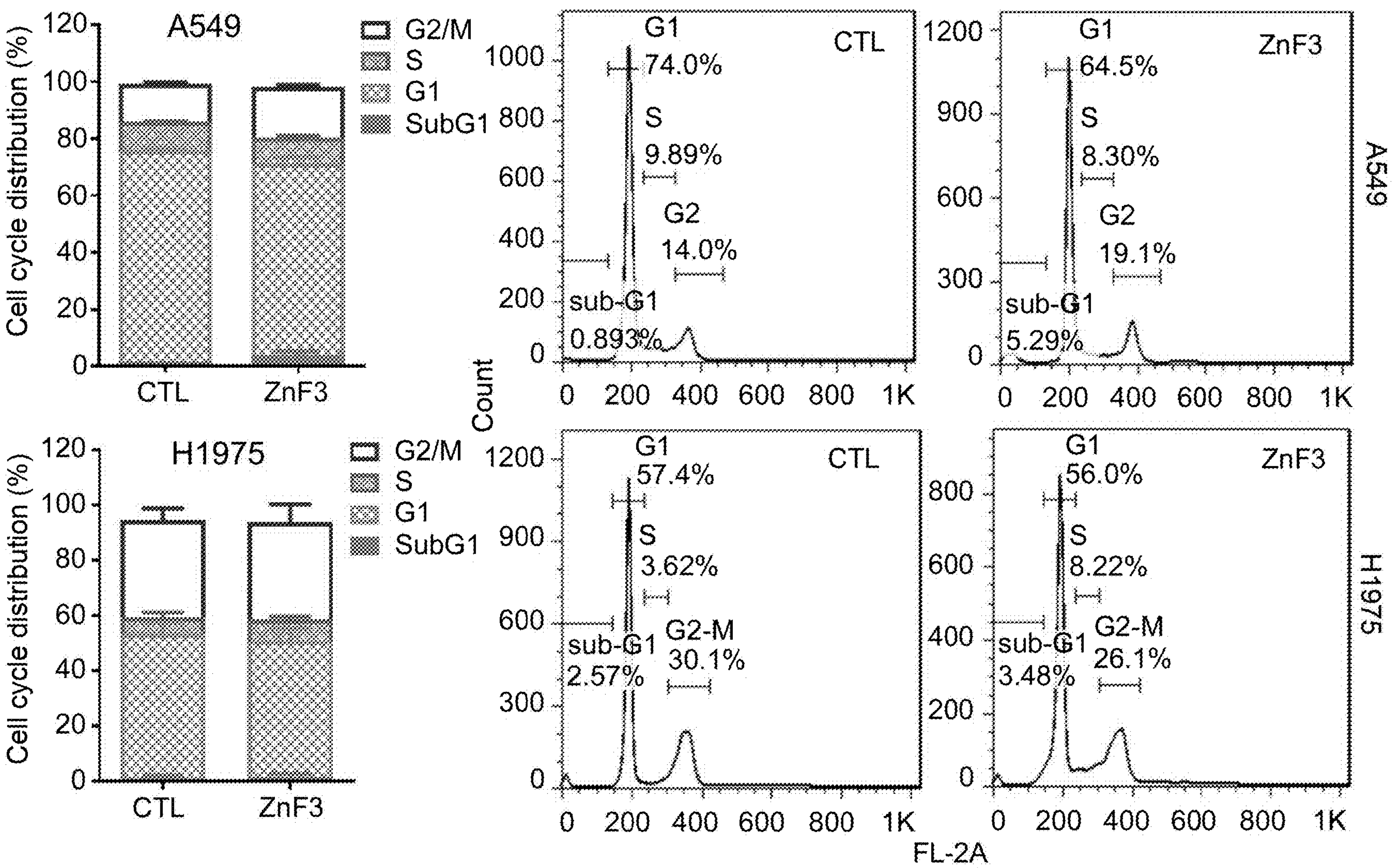

The effect of cell cycle arrest by ZnF3 was further determined. For example, cells ($4\times10^5$ cells/well) were treated with ZnF3 at 400 μg/mL for 48 h at 37° ° C. The procedure for cell cycle analysis is described previously. Briefly, cells after ZnF3 treatment were harvested and stained with PI master mixture buffer (PBS 50 μL, PI 100 μg/mL and RNase 10 μL (Sigma-Aldrich, USA)) at 37ºC for 30 min. Then, flow cytometry (BD FACSCalibur) was used to determine the effect of ZnF3 on cell cycle distribution in A549 and H1975 cells. As shown in FIG. 4B, ZnF3 increases the proportion of cells in the subG1 and G2/M phase, compared to the control groups in A549 cells. ZnF3 also induces subG1 and G2/M population in H1975 cells.

In addition, an AnnexinV/PI assay was used to determine apoptosis response induced by ZnF3 in lung cancer cells due to induction of subG1 arrest. Briefly, cancer cells ($1\times10^5$ cells/well) were seeded in 12-well plates and harvested by trypsinization after 48 h treatment with ZnF3. The procedure for apoptosis analysis was described previously. Briefly, the suspended cells were stained using an Alexa Fluor 488 Annexin V Apoptosis Kit (Life Technologies) for 30 min in dark. Apoptotic cells were detected by flow cytometry (BD FACSCalibur) and analyzed using FlowJo 7.6.1 software.

Figure 4C:
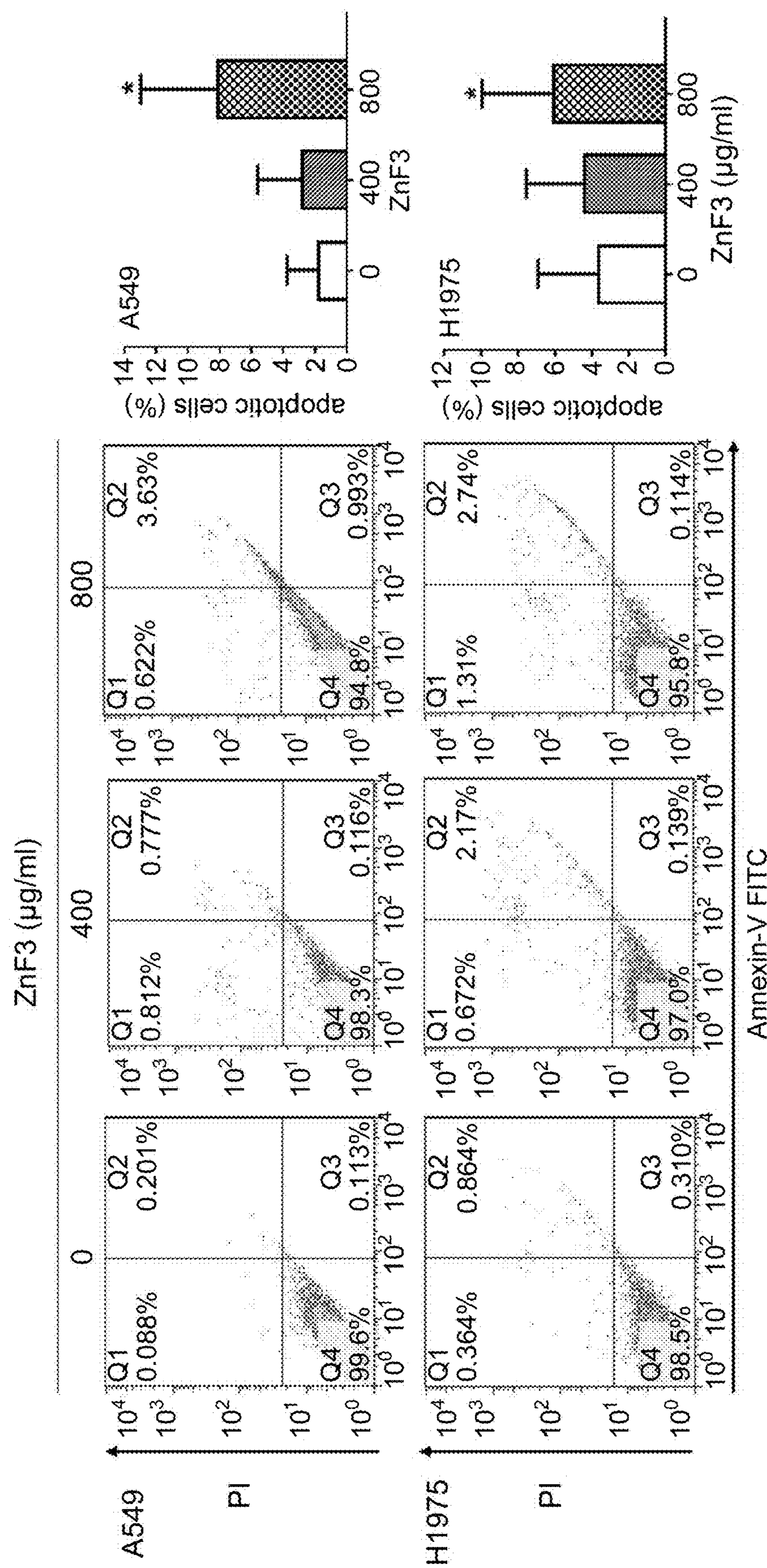
Figure 5:
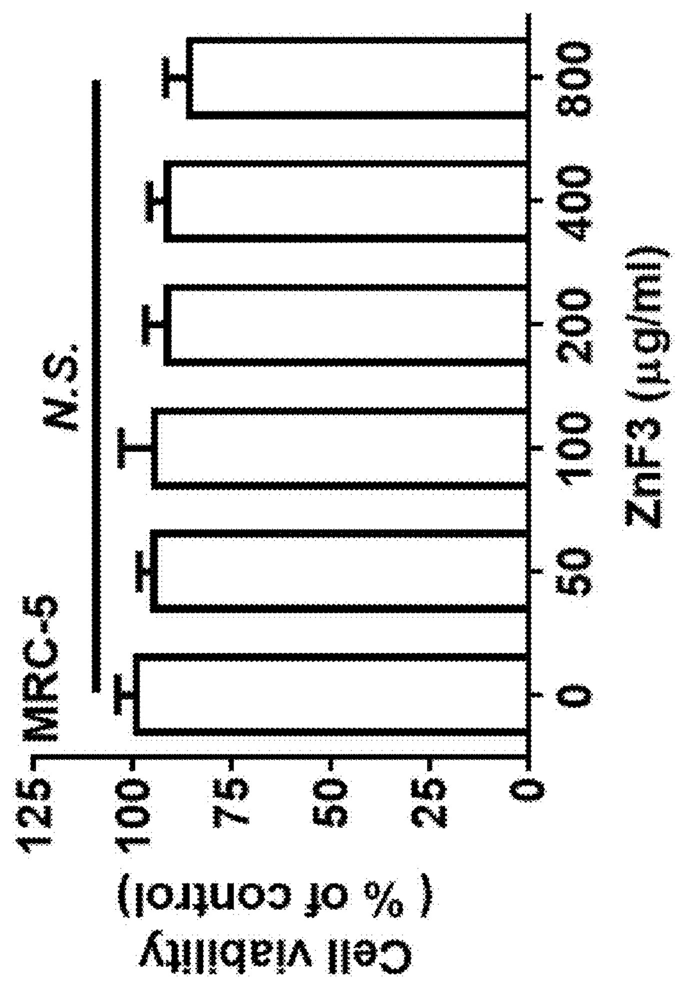
FIG. 5 shows that ZnF3 does not affect cell viability of human normal lung MRC-5 cells. MRC-5 cells were treated with ZnF3 (0 to 800 μg/mL) for 48 h. The cell viability was then determined using MTT assay. Each group of ZnF3-treated samples was normalized against an untreated control group. The data were representative of six separated experiments and presented as the mean±SD, and error bars indicated SDs. N.S. stands for not significant.

As shown in FIG. 4C, the percentage of apoptotic cells is significantly increased in cancer cells after ZnF3 treatment. In parallel, the cytotoxicity of ZnF3 on normal lung cell lines was also determined. Normal human lung fibroblast MRC-5 cells were used to determine the cytotoxic effect of ZnF3. As shown in FIG. 5, ZnF3 does not inhibit cell viability for MRC-5 cells after 48 h treatment. Therefore, ZnF3 is a safe anti-cancer agent for inhibiting lung cancer cells by inducing apoptosis in cancer cells without affecting normal cells.

Example 3: ZnF3 Downregulated EGFR and TGFβRI in Cancer Cells

Figure 6A:
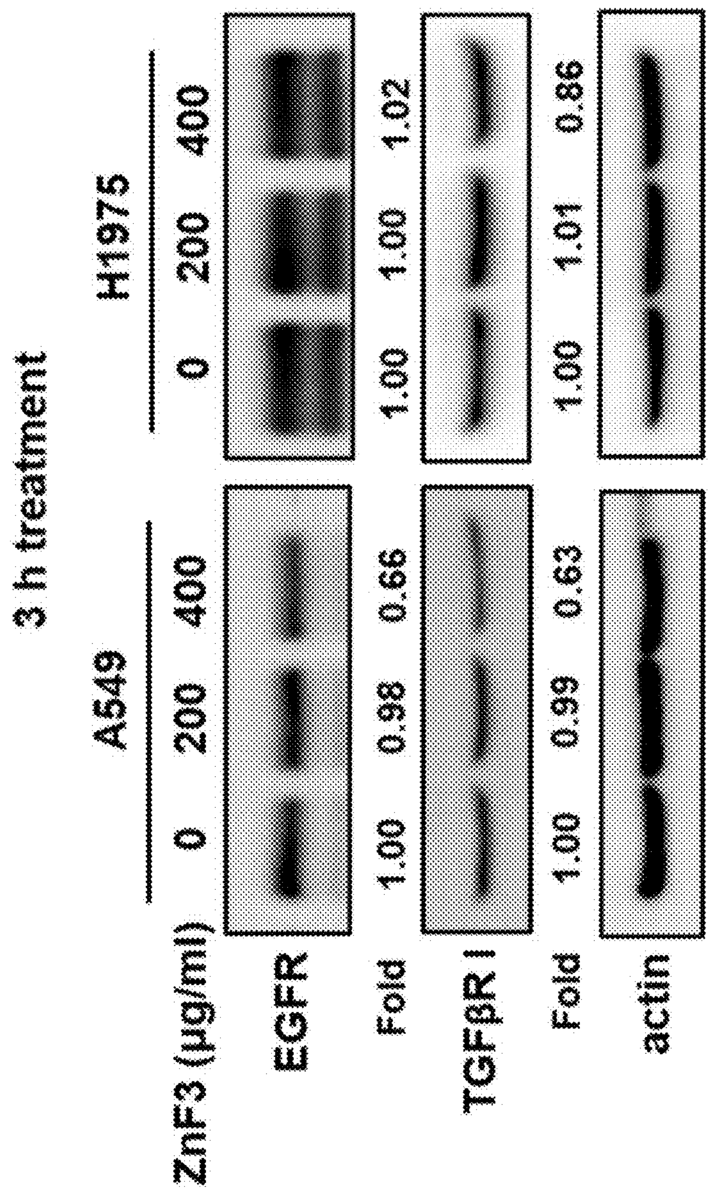
FIGS. 6A and 6B show that ZnF3 downregulates protein levels of EGFR and TGFβRI. A549 and H1975 cells were treated with ZnF3 with indicated concentrations for 3 h (FIG. 6A) and 24 h (FIG. 6B). After treatment, whole lysates were collected, and Western blotting was used to detect protein levels of EGFR and TGFβRI. Actin was used as the loading control.
Figure 6B:
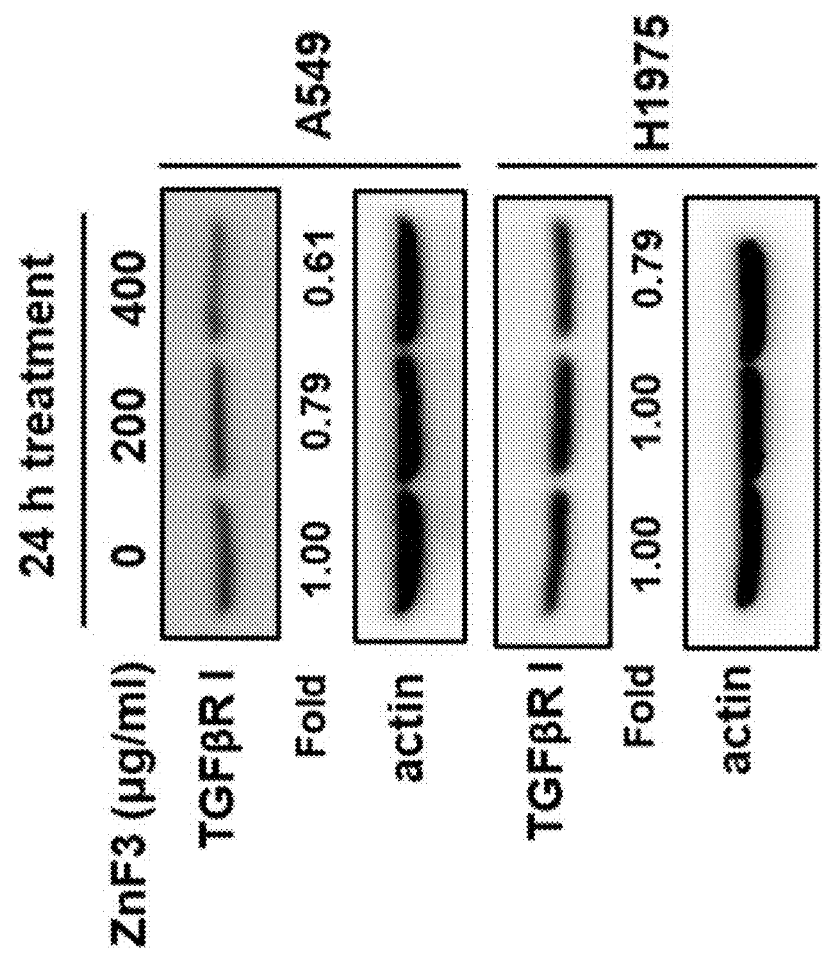

As shown in Table 1 above, ZnF3 is a glucose-rich SPS with a high percentage of mannose. It was found that ZnF3 possesses anti-cancer activity. ZnF3's role in inducing changes in the protein levels of EGFR and TGFβRI is investigated by Western blot assay following standard protocols. The antibodies against EGFR, TGFβRI and actin were purchased from GeneTex (Hsinchu, Taiwan). As shown in FIG. 6A, Western blot assay using the cell lysates harvested from cancer cells treated with ZnF3 for 3 hours shows that ZnF3 decreases EGFR levels in A549, which is a cancer cell line having wild-type EGFR. Also shown in FIG. 6A, ZnF3 downregulates levels of TGFβRI in both A549 and H1975 cells in a concentration-dependent manner. Longer treatment using ZnF3 for 24 hours in lung cancer cells further decreases the expression of TGFβRI, as shown in FIG. 6B. These results show that SPS isolated from *A. cinnamomea* suppresses cancer cells through downregulation of TGFβRI.

Example 4: ZnF3 Activated Macrophage Via Induction of Cytokines and Phagocytosis Activated macrophages increase the production of pro-inflammatory factors, such as NO, TNF-α, IL-1β and IL-6, thereby killing bacteria and cancer cells. Here, the effects of ZnF3 on macrophage activation were studied.

Figure 7B:
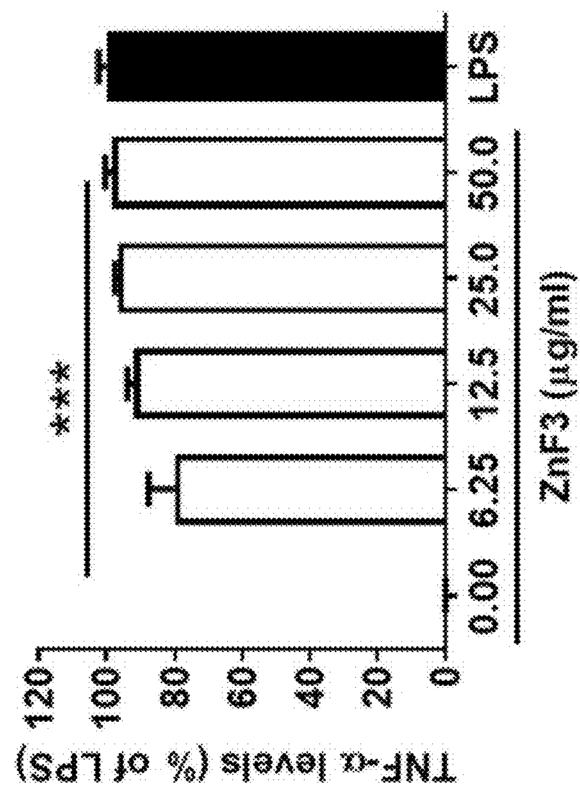
FIGS. 7A to 7G show that ZnF3 activates macrophage Raw264.7 cells. Raw264.7 cells were treated with various concentrations of ZnF3 (0 to 50 μg/mL) for 24 h, and LPS stimulation of Raw264.7 cells at 0.1 μg/mL was used as the positive control.
Figure 7A:
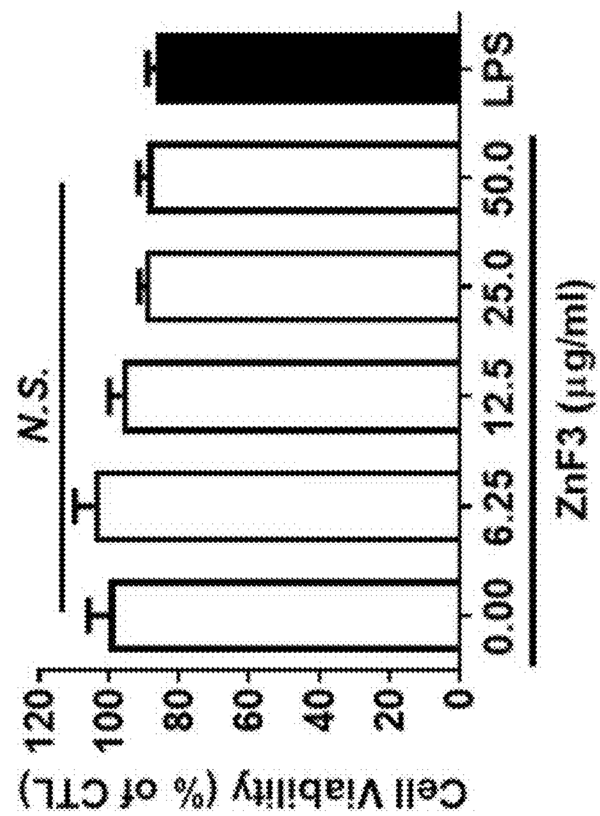

The cell viability of Raw264.7 after treated with ZnF3 or LPS was determined. Briefly, Raw264.7 cells were treated with various concentrations of ZnF3 (0 to 50 μg/mL) or stimulation of LPS (0.1 μg/mL; *E. coli* 055:B5; Sigma Chemical L 2630, St. Louis, MO, USA) for 24 h before evaluation of the effects of treatments on cell viability. As shown in FIG. 7A, ZnF3 at 50 g/mL for 24 h slightly reduces the viability of Raw264.7 cells, similar to stimulation of LPS.

Figures 7C, 7D:
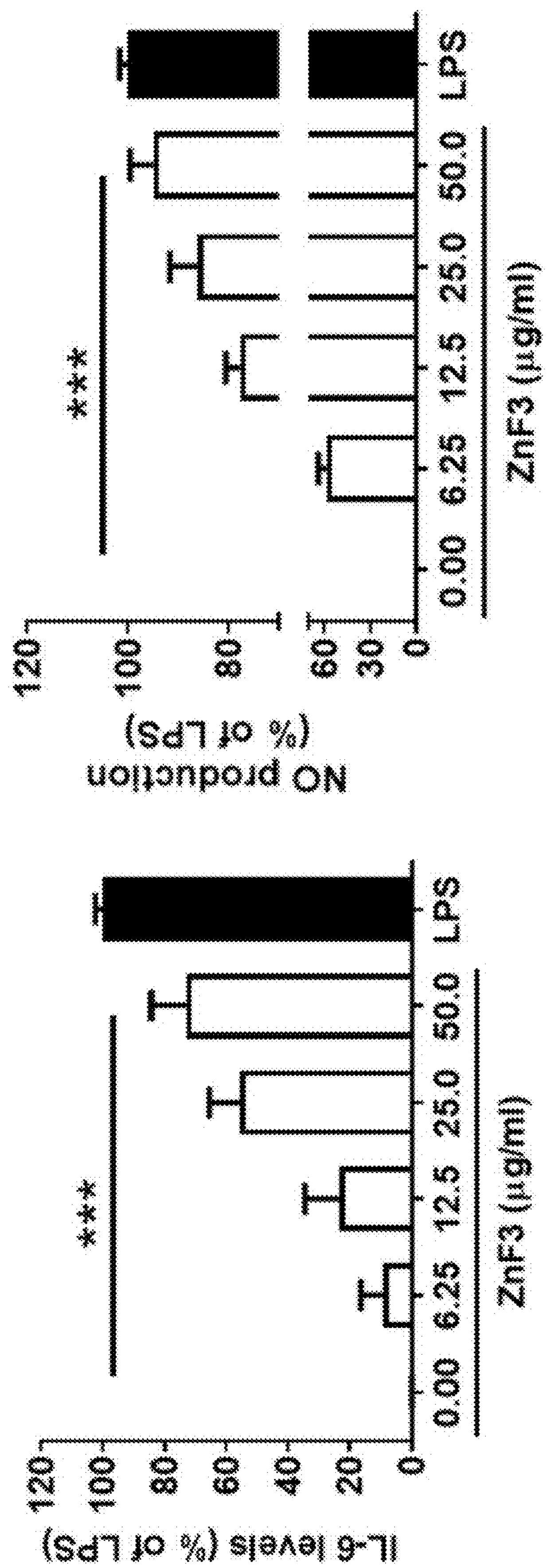

Raw264.7 cells were incubated with LPS (0.1 μg/mL) or ZnF3 at a concentration of 6.25, 12.5 and 50 μg/mL for 24 h and measured for the levels of TNF-α and IL-6 in the cultured medium of Raw264.7 cells using an Enzyme-Linked Immunosorbent Assay (ELISA) Kit (BioLegend, San Diego, CA, USA) according to the manufacturer's instructions. Standard curves for the assay system were obtained for a series of dilutions of the TNF-α and IL-6 (from 0 to 1,000 μg/mL). A 450/550 nm was determined using a TECAN Sunrise ELISA Reader (Tecan Group Ltd., Männedorf, Switzerland). As shown in FIGS. 7B and 7C, ZnF3 induces a significant increase in levels of TNF-α and IL-6 compared to untreated cells, and macrophages treated with 50 μg/mL show similar levels of TNF-α to that in LPS stimulation.

The yield of NO was measured using a Griess assay as described in Sun et al., Sensors 3(8) (2003) 276-284. Briefly, the culture medium of Raw264.7 cells was incubated with the Griess reagent for 10 min, and the optical density was measured at 540 nm. $NaNO_2$ was used to generate a standard curve, and the level of NO from Raw264.7 cells by LPS stimulation was taken as 100%. As shown in FIG. 7D, ZnF3 induces significant NO production in a dose dependent manner.

Figure 7E:
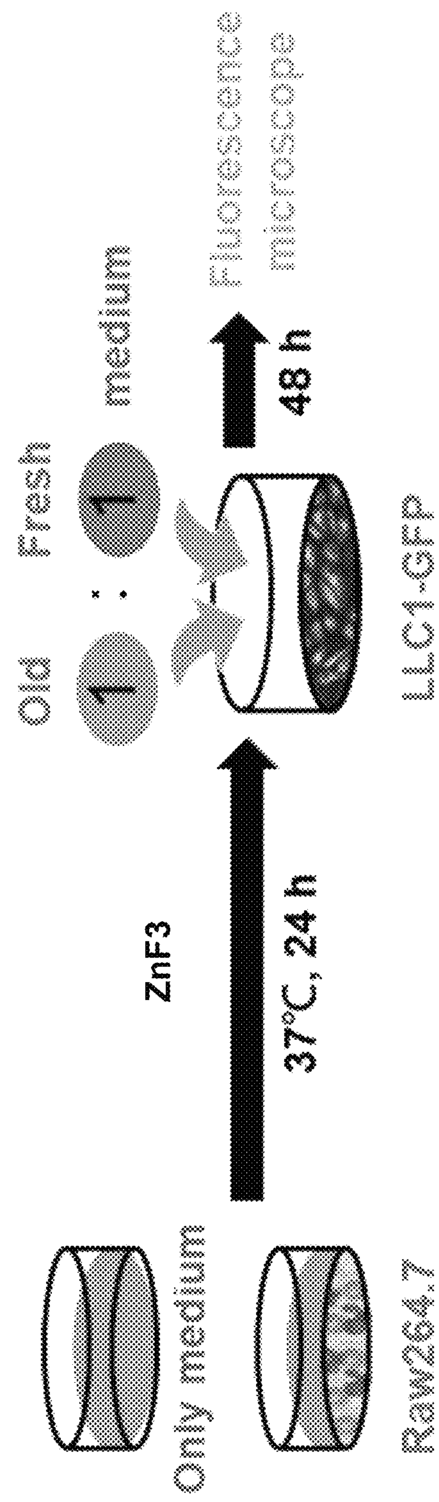
Figure 7F:
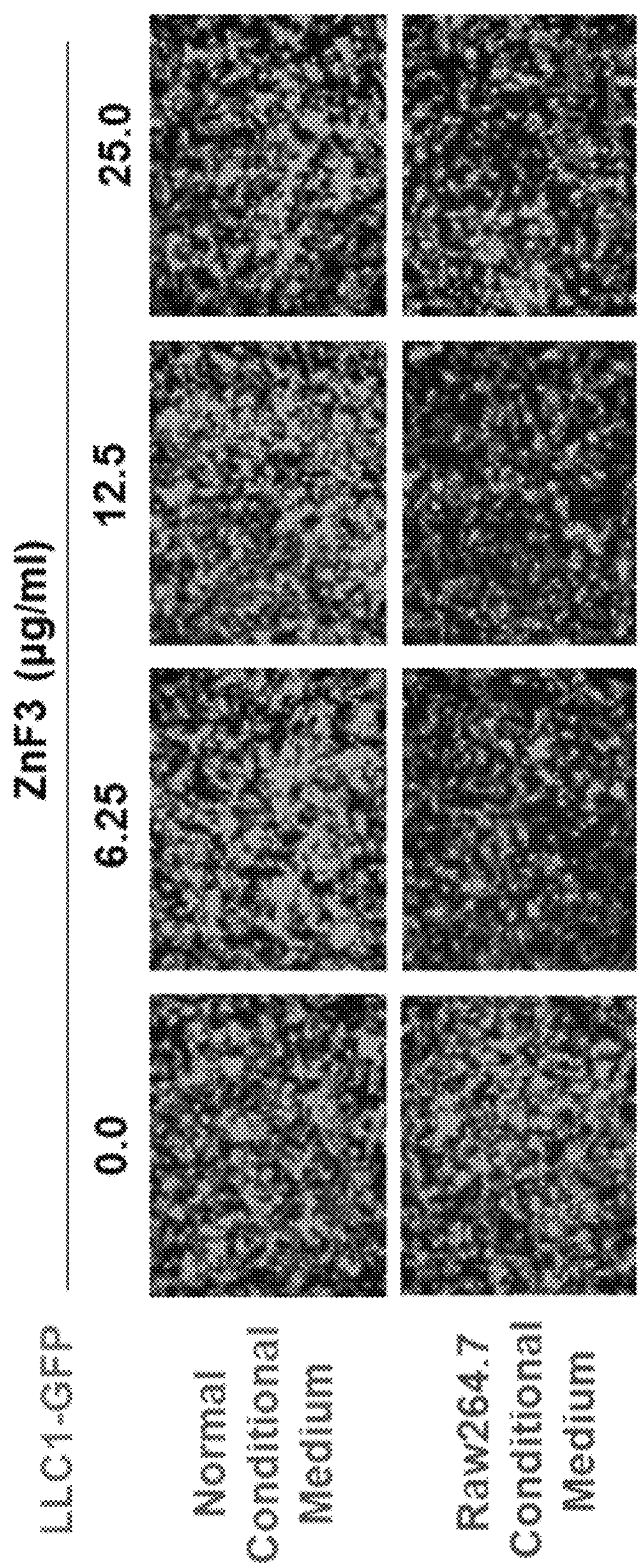
Figure 7G:
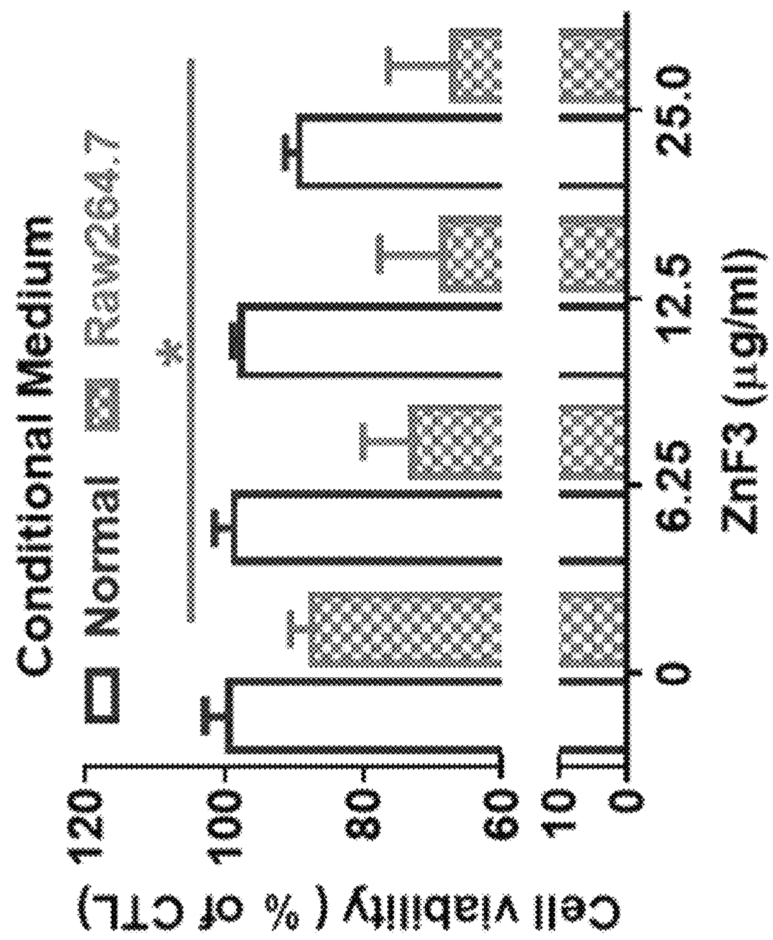

Furthermore, green-fluorescence (GFP) stable murine Lewis lung carcinoma (LLC1-GFP) cells were conducted to determine the effect of ZnF3-stimulated Raw264.7 on cell viability of LLC1-GFP. As shown in the experimental scheme in FIG. 7E, LLC1-GFP cells were treated with a conditional medium, which includes cytokines produced by ZnF3-stimulated macrophages. The results show that the conditional medium from ZnF3-stimulated macrophages inhibits cell viability of lung cancer LLC1 cells, with a cell viability inhibition of about 25% to 30%, as shown in FIGS. 7F and 7G.

Figure 8A:
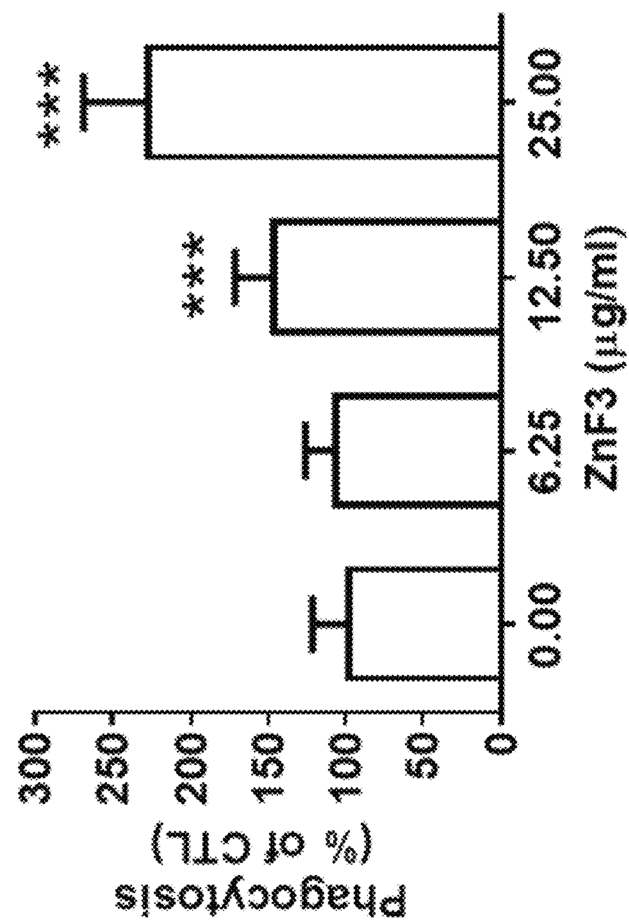
FIGS. 8A to 8D show that ZnF3 increases phagocytosis of macrophage Raw264.7 cells.
Figure 8B:
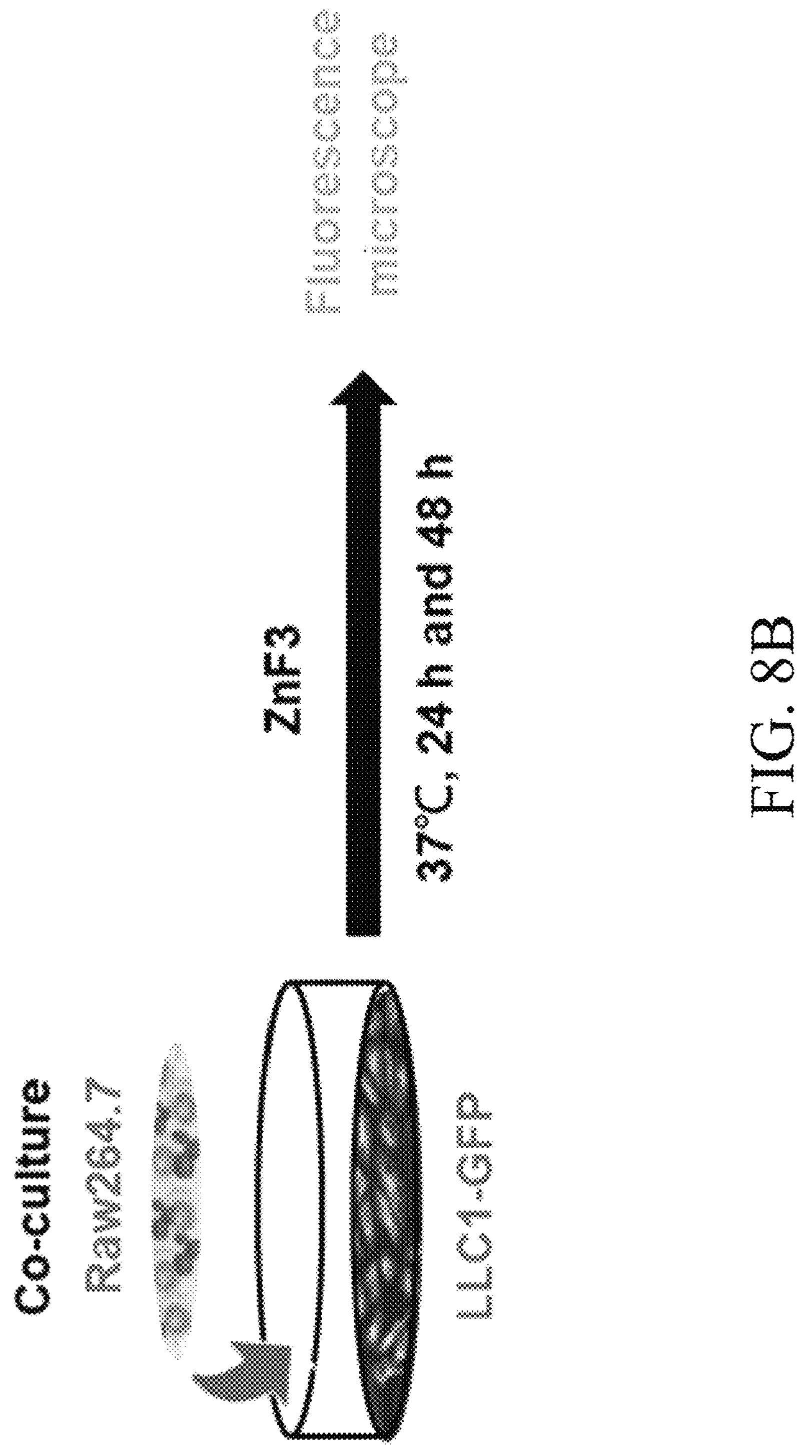
Figure 8C:
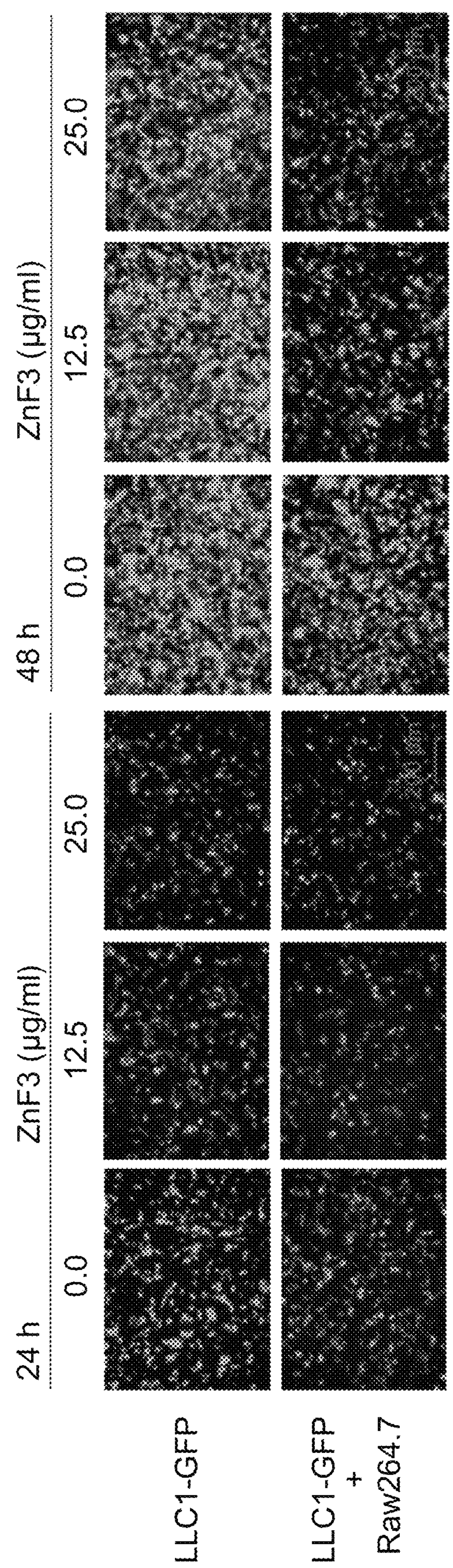
Figure 8D:
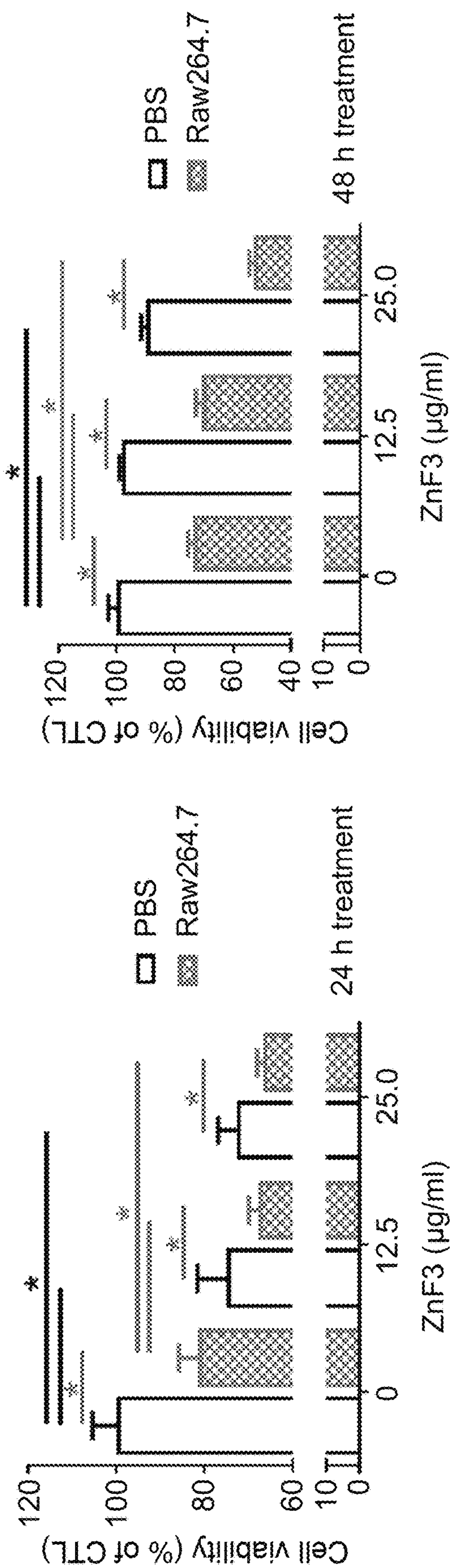

Moreover, it is shown that ZnF3-stimulated Raw264.7 cells directly affect cell viability of LLC1-GFP cells. For example, ZnF3 induces phagocytosis of a macrophage as shown in FIG. 8A. A co-culture experiment of Raw264.7 and LLC1-GFP cells as shown in FIG. 8B was performed to determine the role of ZnF3 on cancer immunotherapy. FIGS. 8C and 8D show that cell viability of LLC1-GFP is decreased as co-cultured with ZnF3-stimulated macrophages. For example, macrophages significantly inhibit the cell viability of LLC1-GFP by up to 50% after 48 h of co-cultivation with ZnF3 at a concentration of 25 μg/mL. These results show that ZnF3 exhibits anti-cancer activity, at least in part by stimulating the activation of macrophage.

Example 5: ZnF3 Enhances M1 Macrophage Polarization

RAW264.7 cell were treated with ZnF3 (25 μg/ml) for 24 h and then detected the surface marker by flow cytometry. Then, CD86, CD80, CD64, and MHCII were used as M1-type macrophage markers. To detect the cell-surface expression of indicated markers, RAW264.7 cells were seeded into the 24-well plate ($5\times10^4$/per well) for 24 h and then treated with ZnF3 (25 μg/ml) for another 24 h. After that, cells were scraped and re-suspended in PBS containing 2% FBS. Next, suspension cells were stained with the CD16/CD32 antibody for 10 min, and then stained with indicated surface marker antibodies for another 30 min. Stained cells were detected by flow cytometry (Beckman CytoFLEX) to analyze the polarization of macrophages. The monoclonal antibody against CD16/CD32 was purchased from eBioscience (Thermo Fisher Scientific, USA). The FITC anti-mouse CD86, FITC anti-mouse CD80, PE/DazzleIM594 anti-mouse CD64, PE anti-mouse I-A/I-E and APC anti-mouse CD206 antibodies were purchased from BioLegend.

Figure 9A:
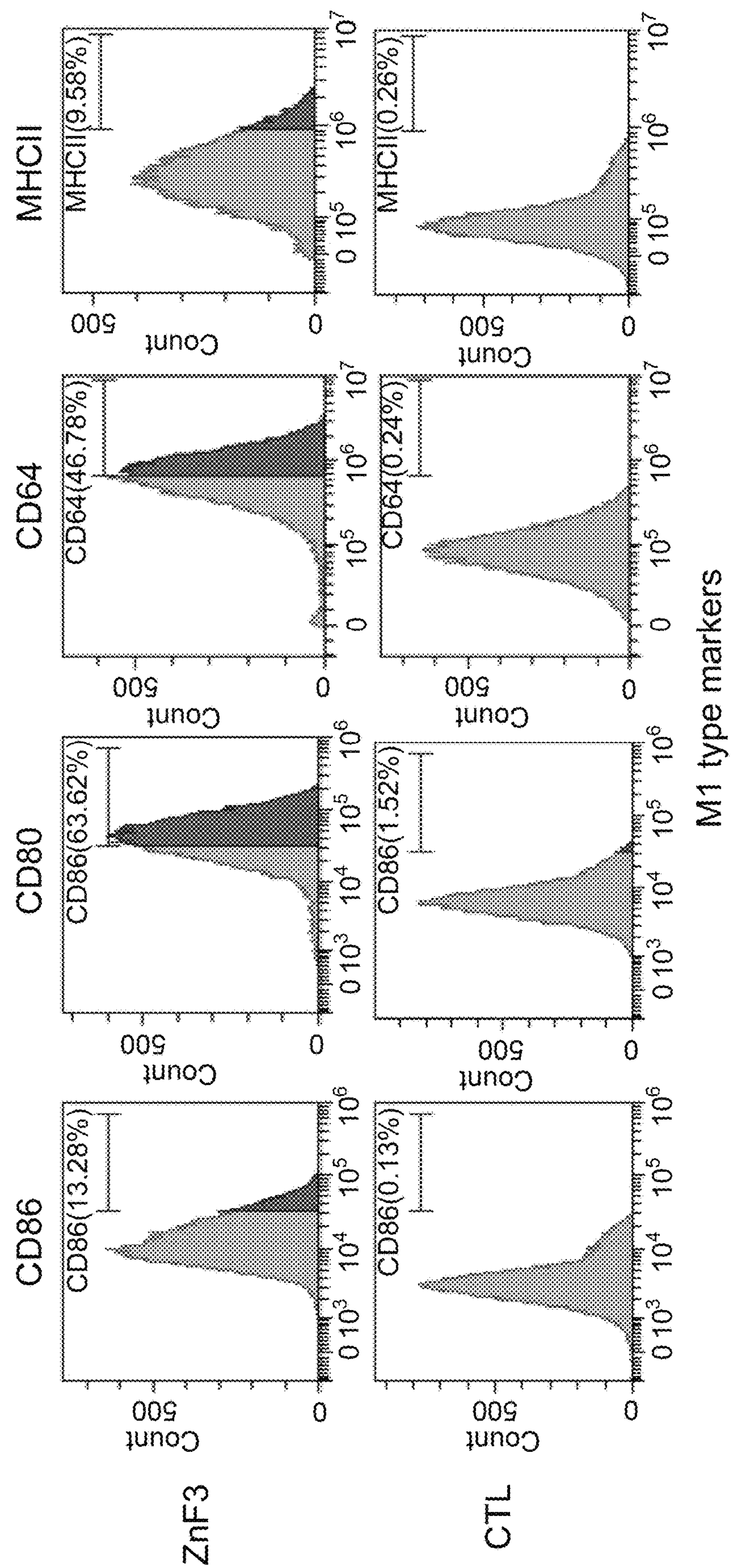
FIGS. 9A to 9C show that ZnF3 increases phagocytosis of macrophage Raw264.7 cells.
Figures 9B, 9C:
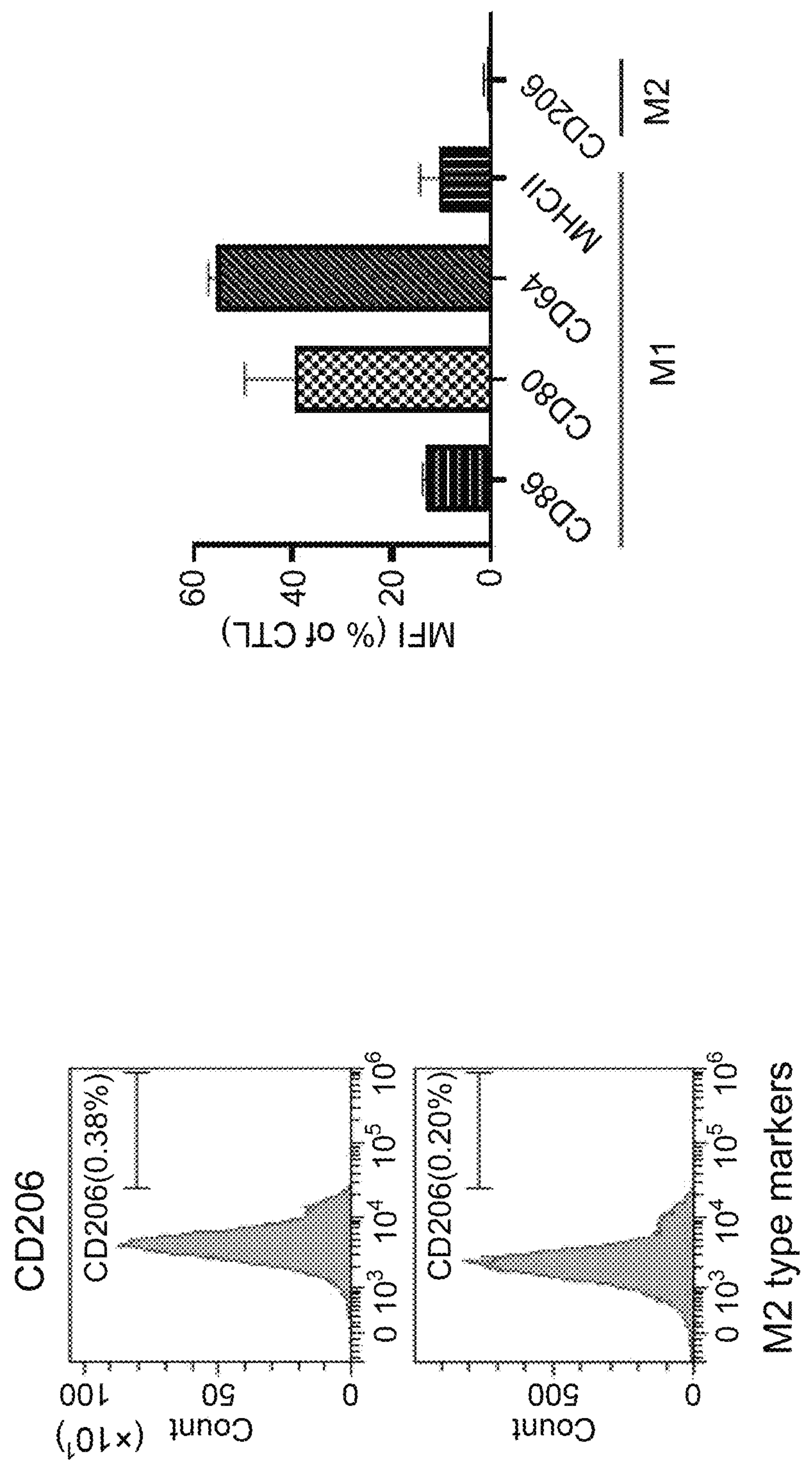

The embodiment of the present application investigated whether ZnF3-stimulated Raw264.7 cells directly affect cell viability for LLC1-GFP cells because ZnF3 could activate macrophage to secret various proinflammatory cytokines. Therefore, whether ZnF3 mediates M1 macrophage polarization in Raw264.7 cells via detecting membrane biomarkers was assessed. As expect, flow cytometry analyses showed that ZnF3 upregulates various M1 type-related markers, such as CD86, CD80, CD64 and MHCII but not M2 type marker CD206 (shown in FIGS. 9A to 9C).

The present disclosure has been described with embodiments thereof, and it is understood that various modifications, without departing from the scope of the present disclosure, are in accordance with the embodiments of the present disclosure. Hence, the embodiments described are intended to cover the modifications within the scope of the present disclosure, rather than to limit the present disclosure. The scope of the claims therefore should be accorded the broadest interpretation so as to encompass all such modifications.

What is claimed is:

1. A method for treating cancer, comprising administering to a subject in need thereof a composition comprising an effective amount of a fraction of polysaccharide isolated from *Antrodia cinnamomea* cultured in the presence of zinc sulfate and a pharmaceutical carrier thereof, wherein the polysaccharide comprises glucose and fucose;

wherein the polysaccharide is sulfated polysaccharide; and wherein the cancer involves signal transduction through EGFR, TGFβRI or a combination thereof.

2. The method of claim 1, wherein the zinc sulfate is between 1 μM to 100 μM.

3. The method of claim 1, wherein the sulfated polysaccharide comprises at least one of galactosamine, glucosamine, galactose, and mannose.

4. The method of claim 3, wherein the glucose has the highest weight ratio in the sulfated polysaccharide.

5. The method of claim 4, wherein a weight ratio of the glucose to the fucose is 1,000:1 to 150:1.

6. The method of claim 4, wherein the sulfated polysaccharide comprises the galactosamine, and a weight ratio of the glucose to the galactosamine is 3,000:1 to 250:1.

7. The method of claim 4, wherein the sulfated polysaccharide comprises the glucosamine, and a weight ratio of the glucose to the glucosamine is 80:1 to 25:1.

8. The method of claim 4, wherein the sulfated polysaccharide comprises the galactose, and a weight ratio of the glucose to the galactose is 10:1 to 20:1.

9. The method of claim 4, wherein the sulfated polysaccharide comprises the mannose, and a weight ratio of the glucose to the mannose is 200:1 to 20:1.

10. The method of claim 1, wherein the polysaccharide has a molecular weight between 1 kDa and 100 kDa.

11. The method of claim 1, wherein the cancer is lung cancer, lung adenocarcinoma, non-small cell lung adenocarcinoma, gastric cancer, urothelial carcinoma, breast cancer, brain cancer, glioma, renal cancer, head and neck cancer, colorectal cancer, or any combination thereof.

12. The method of claim 1, wherein the cancer has wild-type EGFR.

13. The method of claim 1, further comprising contacting an immune cell with the composition to activate the immune cell.

14. The method of claim 13, wherein the immune cell is a phagocyte.

15. The method of claim 13, wherein the immune cell is neutrophil, monocyte, macrophage, mast cell, or dendritic cell.

* * * * *